(12) United States Patent
Naji

(10) Patent No.: US 9,483,807 B2
(45) Date of Patent: Nov. 1, 2016

(54) HOSPITAL COMMUNICATION SYSTEM

(75) Inventor: Mohammed Naji, Riverside, CA (US)

(73) Assignee: LAGUNA MENA INC, Covina, CA (US)

( * ) Notice: Subject to any disclaimer, the term of this patent is extended or adjusted under 35 U.S.C. 154(b) by 351 days.

(21) Appl. No.: 12/411,915

(22) Filed: Mar. 26, 2009

(65) Prior Publication Data

US 2010/0250270 A1  Sep. 30, 2010

(51) Int. Cl.
*G06Q 50/22* (2012.01)
*G06Q 10/10* (2012.01)

(52) U.S. Cl.
CPC ............ *G06Q 50/22* (2013.01); *G06Q 10/109* (2013.01)

(58) Field of Classification Search
USPC .......................................................... 705/2–3
See application file for complete search history.

(56) References Cited

U.S. PATENT DOCUMENTS

| | | | |
|---|---|---|---|
| 4,937,743 A * | 6/1990 | Rassman et al. ............ 705/7.22 |
| 5,098,426 A | 3/1992 | Sklar et al. | |
| 5,748,907 A | 5/1998 | Crane | |
| 5,822,544 A | 10/1998 | Chaco et al. | |
| 5,842,173 A | 11/1998 | Strum et al. | |
| 5,983,749 A | 11/1999 | Holtorf | |
| 5,995,937 A | 11/1999 | Debusk et al. | |
| 6,157,914 A | 12/2000 | Seto et al. | |
| 6,179,829 B1 | 1/2001 | Bisch et al. | |
| 6,345,260 B1 | 2/2002 | Cummings et al. | |
| 6,364,834 B1 | 4/2002 | Reuss et al. | |
| 6,526,397 B2 | 2/2003 | Chee et al. | |
| 6,659,947 B1 | 12/2003 | Carter et al. | |
| 6,876,303 B2 | 4/2005 | Reeder et al. | |
| 6,904,318 B2 | 6/2005 | Hill et al. | |
| 7,278,579 B2 | 10/2007 | Loffredo et al. | |
| 2003/0036683 A1* | 2/2003 | Kehr et al. ..................... 600/300 |
| 2005/0033603 A1* | 2/2005 | Suzuki et al. ..................... 705/2 |
| 2005/0060246 A1* | 3/2005 | Lastinger .......... G06K 17/0022 705/28 |
| 2005/0165454 A1 | 7/2005 | Chinchoy | |
| 2006/0116667 A1* | 6/2006 | Hamel .......... A61B 17/320068 606/1 |
| 2008/0084296 A1 | 4/2008 | Kutzik et al. | |
| 2008/0140158 A1* | 6/2008 | Hamel et al. ................... 607/60 |
| 2008/0319275 A1* | 12/2008 | Chiu et al. ................... 600/300 |

FOREIGN PATENT DOCUMENTS

| WO | WO 01/93175 | 12/2001 |
| WO | WO 2008/098085 | 8/2008 |

OTHER PUBLICATIONS

Argawal, Sheetal, et al., A Pervasive Computing System for the Operating Room of the Future, Mobile Networks and Applications, 2007, vol. 12, pp. 1-18.*

* cited by examiner

*Primary Examiner* — Amber A Misiaszek
(74) *Attorney, Agent, or Firm* — Jafari Law Group, Inc.

(57) ABSTRACT

The invention is a hospital scheduling system that allows for real-time updates of the status of a medical procedure to be transmitted. More particularly, this transmission allows for the consistent flow of a pre-arranged sequence of events a hospital may use for patient treatment procedures. Once an event has transpired, notice of the event occurrence may be transmitted to interested personnel through specific transmission, or a general broadcast for all personnel such that updates may be checked by any interested hospital personnel. The devices capable of receiving the transmissions may be a wired device, or may be a portable wireless device, such as a hand-held unit. Moreover, the invention describes a pedal that may be capable of programming such that when specific areas of the pedal are compressed, coding will be sent to a computer for translation into status messages that may be transmitted through a network to any number of recipients. The pedal may be adapted such that compressions may be performed by the user's foot.

16 Claims, 9 Drawing Sheets

HOSPITAL COMMUNICATION SYSTEM

TECHNICAL FIELD OF THE INVENTION

The present invention relates in general to a hospital scheduling system, and more specifically, to a system for receiving real-time updates of the status in medical procedures.

COPYRIGHT & TRADEMARK NOTICE

A portion of the disclosure of this patent application may contain material that is subject to copyright protection. The owner has no objection to the facsimile reproduction by any one of the patent document or the patent disclosure, as it appears in the Patent and Trademark Office patent file or records, but otherwise reserves all copyrights whatsoever.

Certain marks referenced herein may be common law or registered trademarks of third parties affiliated or unaffiliated with the applicant or the assignee. Use of these marks is by way of example and shall not be construed as descriptive or to limit the scope of this invention to material associated only with such marks.

BACKGROUND OF THE INVENTION

Operating rooms are organized such that several patients will be scheduled for an operating room in a given day. Many tasks are necessary for a surgery, and operating room specialists must coordinate their work in order to ensure efficiency and smooth transitions between tasks. Each task requires the allocation of specific resources, and when the tasks are delayed costs may rise (for example if the surgical team is waiting around they are being paid but there is no patient care being provided to offset the costs). Lack of coordination results in errors, misunderstandings between personnel, excess costs, and wastes of time. Therefore, surgical personnel are responsible for implementing a systematic work plan for surgical procedures.

During the course of patient treatment there are several different "steps" in the care provided. Each of these steps corresponds to a different point in the timeline of the surgical procedure, and thus can be identified as the "status" of the patient's treatment. Preliminary preparation of the operating room is done before the patient enters. Cleaning the operating room is part of total patient care and is a cooperative effort involving several personnel members, each with separate duties. The division of duties is quite specific, yet each member must plan the timing of their duties such that both the sterile and nonsterile parts of the operation move along expeditiously.

Definite routines are established for the preparation of an operating room for surgery. To work efficiently during a surgical procedure, personnel must be thoroughly familiar with the established routine in the operating room suite. Once a sequence is established, each surgical team member must be aware of what steps have already been taken to know when they must perform their steps of the sequence. Failure to communicate the status of each surgical routine step causes unnecessary delay and extraneous costs.

The current system for the timely implementation of multiple surgical procedures involves a back-and-forth between different surgical personnel teams. For example, surgery A is to be performed with surgery B following immediately afterwards once the operating room has been cleaned and prepared. Surgeries can last anywhere from minutes to hours, and usually the time for a specific surgery will vary somewhat with each surgeon that performs the surgery, and with each patient on which it is performed. Thus, in order for the surgeon performing surgery B to know when the room is cleared and prepared, the surgeon must continually call a nurse or assistant stationed near the room to check on the status of surgery A. Unfortunately, there is often no one available to answer the phone, or the person giving an update is unaware of a change in the status of the surgical procedure, and available operating rooms go unused while hospital personnel wait around needlessly. This causes unnecessary excess costs in patient care, and diminishes the efficiency of the surgical process.

Systems have been developed for the storing of hospital data and patient medical information; however they do not promote real-time communication of the status of medical procedures. Typical systems consist of hand-written notes taken by the medical personnel during the procedure, which are then entered into a computer system later in the day. Thus, there is a need in the art for a system of intra-hospital communication that would deliver real-time status updates. Specifically, there is a need for a system that is able to inform hospital personnel what steps are in process during a medical procedure, particularly in a room that requires sterility, so as to efficiently schedule subsequent hospital procedures. It is to these ends that the present invention has been developed.

SUMMARY OF THE INVENTION

To minimize the limitations in the prior art, and to minimize other limitations that will be apparent upon reading and understanding the present specification, the present invention describes a medical communication system and device for the transmission of status updates in "real-time".

A method in accordance with the present invention comprises on-going medical procedures to be performed which consist of the following steps: preparation or set-up of the treatment site, the treatment of the patient, observation of the patient after treatment, and clean up of the treatment site including preparation for a subsequent medical treatment to be performed. The method also includes a network adapted to transmit the status of the medical procedure being performed. The system does so by sending the status with respect to the step of the procedure engaged in with real-time updates.

It is an objective of the present invention to promote real-time communication of the status of medical procedures to hospital personnel for immediate time-management updates by sending a limited broadcast to specific recipients via a medical computer network.

It is another objective of the present invention to provide a system that is able to inform hospital personnel regarding the steps that are in process during a medical procedure, so as to schedule subsequent hospital procedures with maximum efficiency. This is advantageous particularly in a room that requires sterility, as personnel then do not have to intrude on the treatment site in order to receive updates.

Finally, it is yet another objective of the present invention to provide a system that notifies hospital personnel of medical treatment updates such that the expenses associated with medical treatment delays may be curtailed.

These and other advantages and features of the present invention are described herein with specificity so as to make the present invention understandable to one of ordinary skill in the art.

BRIEF DESCRIPTION OF THE DRAWINGS

Elements in the figures have not necessarily been drawn to scale in order to enhance their clarity and improve understanding of these various elements and embodiments of the invention. Furthermore, elements that are known to be common and well understood to those in the industry are not depicted in order to provide a clear view of the various embodiments of the invention.

DETAILED DESCRIPTION OF THE DRAWINGS

In the following discussion that addresses a number of embodiments and applications of the present invention, reference is made to the accompanying drawings that form a part hereof, where depictions are made, by way of illustration, of specific embodiments in which the invention may be practiced. It is to be understood that other embodiments may be utilized and changes may be made without departing from the scope of the present invention.

Figure 1A:
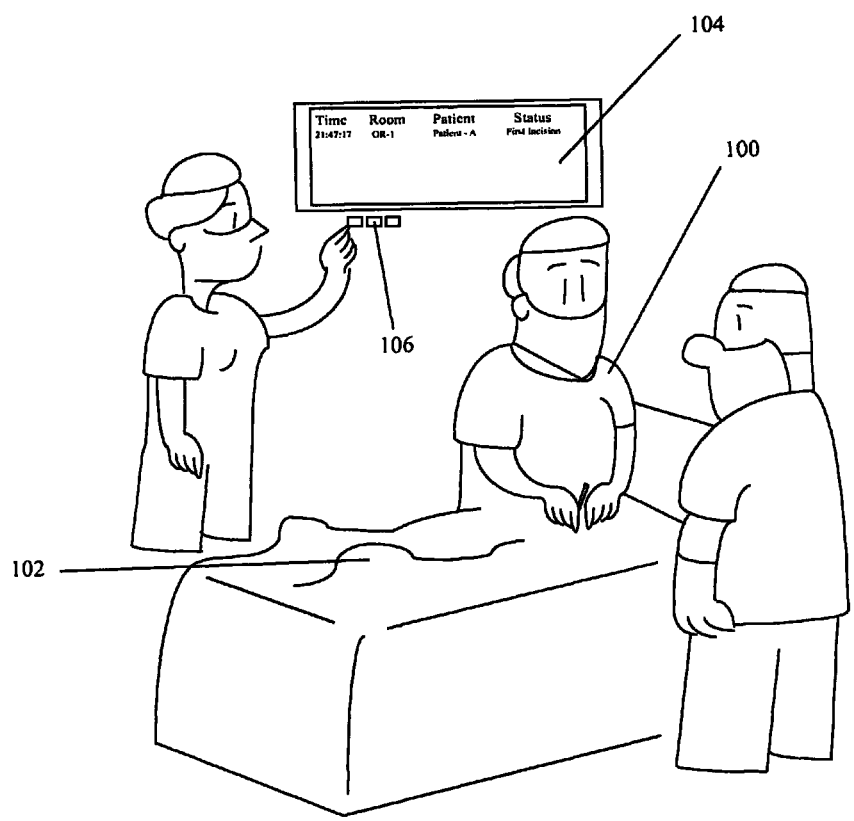
FIG. 1(a) illustrates a status information communication about an on-going medical procedure being sent by medical personnel through a medical display device.

FIG. 1(a) illustrates a status information communication about an on-going medical procedure being sent by medical personnel through a medical display device. FIG. 1(a) shows a doctor 100, with or without supporting staff, performing a medical procedure upon Patient 102. The doctor, or another member of the support staff, may then transmit a real-time status information communication about the on-going medical procedure by activating a medical communication device 104. The status information may be transmitted by pressing button 106 on the medical communication device, pre-programmed to send a specific status update.

"Transmission" in an exemplary embodiment includes sending the status update of a medical procedure being performed. Transmission is sent in "real-time", meaning the status message is sent and received during performance of the medical procedure, and the message corresponds to the actual time during which a process takes place or an event occurs.

The use of a button in this embodiment, however, and should not be read to limit the scope of the present invention. In another embodiment, medical communication device 104 may be a pedal adapted to transmit programmable or set/pre-defined codes depending upon which button or combination of buttons are pressed by a user. In still another embodiment, medical communication device 104 may have electromagnetic or motion sensors that transmit pre-programmed status updates based on the area where motion is detected, or may be voice activated to transmit pre-programmed status updates based upon commands stated by medical staff. Alternatively, medical communication device 104 may comprise a video camera and transmit video images of a surgical operation in progress in the operating room.

Figure 1B:
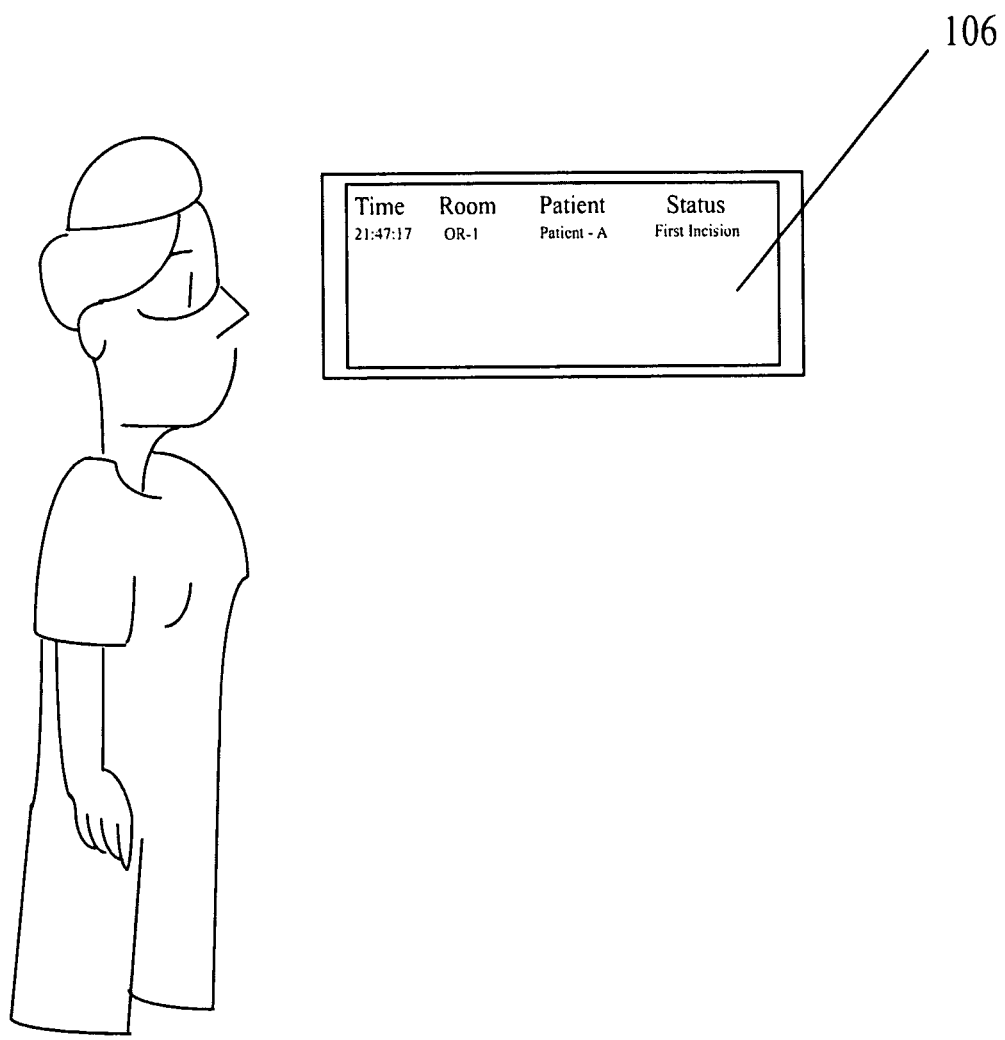
FIG. 1(b) illustrates a status information communication about an on-going medical procedure being received by medical personnel through a medical display device.

FIG. 1(b) illustrates a status information communication about an on-going medical procedure being received by medical personnel through a medical display device.

As illustrated, a status information communication about an on-going medical procedure is received by both medical personnel and a medical display device 106. The medical display device 106 is here embodied as a visual display describing the status of patients undergoing medical procedures. "Reception" constitutes receipt of a status message, as the message may be displayed in real-time. As a result of the reception of a real-time status information communication, the medical display device may update and henceforth display the updated status information with regards to the on-going medical procedure. In an exemplary embodiment, status information may be displayed on a central screen at a fixed location, such as a nurses' station.

In another embodiment of the present invention, status information communications may be sent directly to employee personnel through personal digital assistants (PDA's), or some other compatible electronic device (cell phone, notebook computer, etc.). In such an embodiment, a status information communication may be received and displayed by a compatible electronic device for reception by the hospital employee. In yet another embodiment of the present invention, status information communications may be sent through, and are compatible with, current existing hospital computer software systems, such as hospital admission software, electronic records software packages, pharmacy Pyxis® products, to name a few.

Figure 2A:
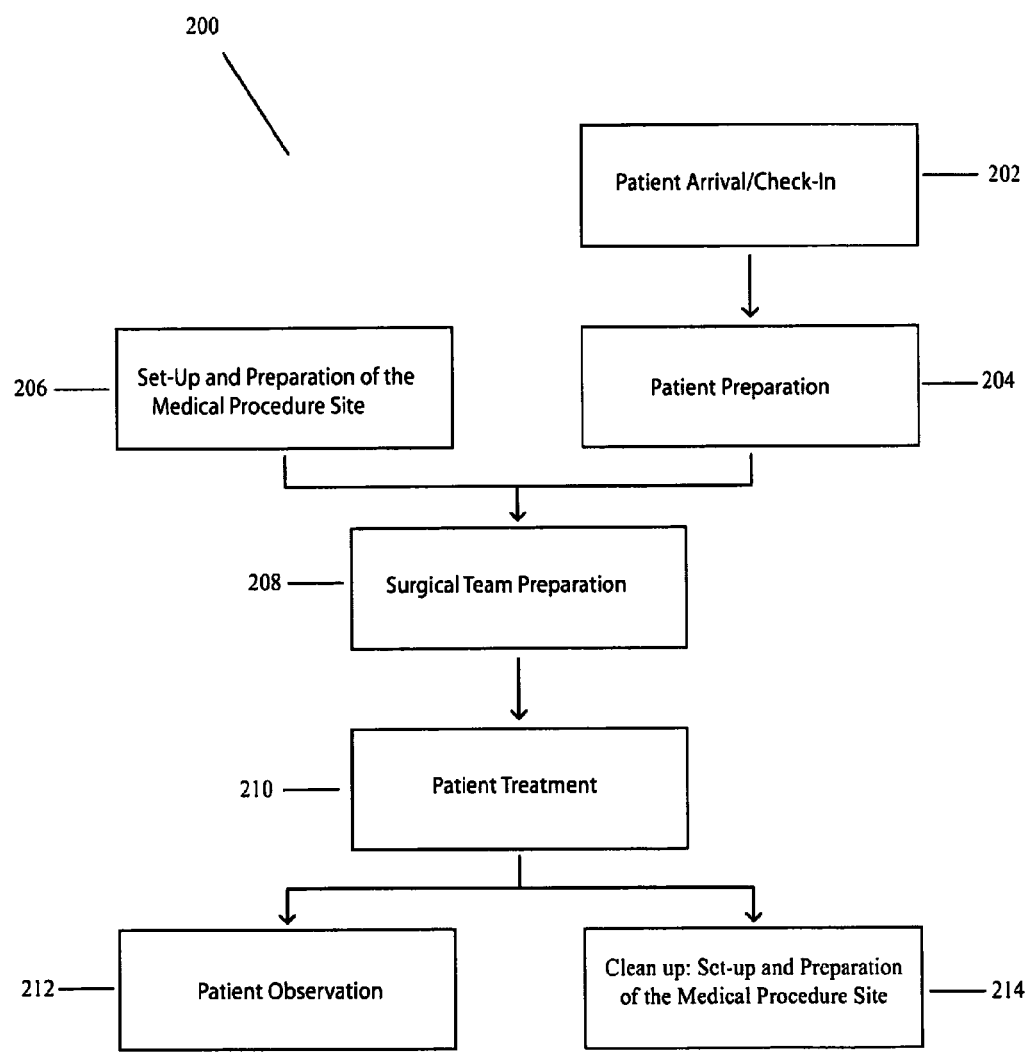
FIG. 2(a) illustrates a flow chart depicting the stages that may comprise a medical procedure.
Figure 2B:
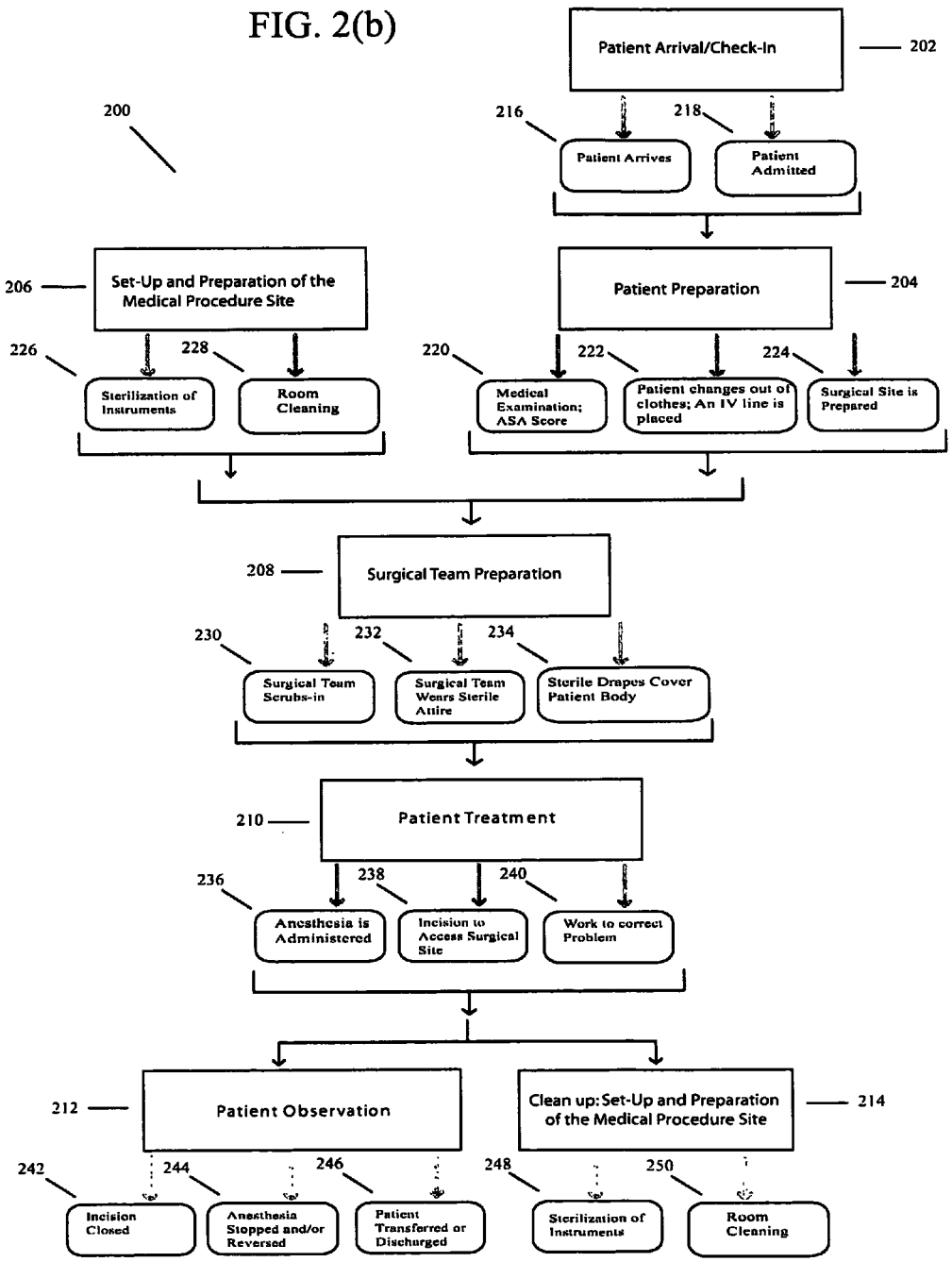
FIG. 2(b) illustrates the sub-elements comprising a medical procedure.

FIG. 2(a) illustrates the stages 200 that may comprise a medical procedure as different elements performed by different hospital personnel. FIG. 2(b) illustrates the sub-elements comprising the different elements or steps of a medical procedure 200.

A medical procedure is performed in a series of events 200 that are done in order based on a routine established by the preferences of hospital personnel. This description analyzes the steps that may comprise a surgical procedure; however, the medical procedure may include any medical treatment comprised of a specific series of events that should be performed in a particular sequence, and as such this description should not be read to be limiting.

The steps of a medical procedure 200 for a surgery may consist of the broad elements of: patient arrival and check-in 202, patient preparation 204, set-up and preparation of the medical procedure site 206, surgical team preparation 208, patient treatment 210, patient observation 212, and clean up with set-up and preparation of the medical procedure site 214. A medical procedure may be "ongoing" if performance may be categorized where the status aspect of any element of a medical procedure routine is in progress.

In an exemplary embodiment of performing the steps 200 of a medical procedure, the patient arrives 202, and the first person the patient encounters may be a staff member working at the reception desk, who may take the patient information. After the patient arrives 216, the patient may be admitted to the surgical ward 218. In a preferred embodiment, the reception staff member may then notify the surgical team (typically including the surgeon, scrub nurse, circulating nurse, surgical technician, and anesthesiologist), who may admit the patient to the hospital or to a surgery center. The surgical nurse, or scrub nurse, primarily specializes in perioperative care (before, during and after the surgery), which may include patient preparation 204. For patient preparation 204, preparation tasks may broadly comprise: explaining procedures to patients, easing patient fears, checking patient vitals, administering medications, and helping to sterilize and mark the surgical site. In an exemplary embodiment, the surgical nurse may send status update messages to the rest of the surgical team for each test or procedure performed during patient preparation 204. To prepare the patient at step 204, a patient may be given a medical examination before the surgery is undertaken 220. A set of vital signs may be recorded (usually by the surgical nurse) and pre-operative tests may be ordered. The American Society of Anesthesiologists has a five-category physical status classification system for assessing the patient before surgery, and the patient may be given an "ASA score" 220. If the results are satisfactory, the patient may then sign a consent form and receive surgical clearance. The patient may then change out of their clothes 222 and may be asked to confirm the details of the surgery. An IV line may be placed 222 so that pre-operative medications may be administered (such as antibiotics and/or sedatives). The surgical nurse may then prepare the surgical site 224 by cleaning the skin surface and preparing it with antiseptic. If hair is present at the surgical site, it may be clipped prior to patient preparation. Once the patient is fully prepared, in an exemplary embodiment the surgical nurse may again notify the rest of the surgical team that the patient is now fully prepared for surgery.

Before steps 200 of a medical procedure are performed, the operating room must be prepared as step 206 illustrates. At step 206, the surgical technician prepares the operating room to ensure it is sterile. This element may involve all instruments being sterilized 226, and the room being cleaned 228. The maintenance staff usually cleans the room, but the technician may oversee the cleaning, and prepare and sterilize instruments to be used. If significant blood loss is expected during the surgery, a blood donation may be gathered. In an exemplary embodiment, once the medical procedure site (which may be an operating room) is prepared, the surgical technician may send a medical procedure update status message to fellow members of the present surgical team, in addition to members of possible subsequent surgical teams, notifying them of the operating room preparation status. This minimizes the waiting time for the medical procedure site to become available, and thus may help to reduce costs of a medical procedure.

The surgical team may prepare themselves at step 208 by "scrubbing-in" 230. In a preferred embodiment this is performed by the surgical team members first scrubbing their hands and arms with an approved disinfectant agent 230. They may then don sterile attire 232, including scrubs, a scrub cap, a sterile surgical gown, sterile latex gloves and a surgical mask. Sterile drapes may be used to cover the patient's body except for the surgical site and the patient's head 234. An "ether screen" may be formed by clipping drapes to poles to separate the anesthesiologist's unsterile working area from the sterile surgical site. During surgical team preparation 208, the technician may also help prepare surgeons and nurses to enter the sterile environment; supply any equipment that might be needed; transport patients to operating rooms, recovery rooms, intensive care units, or regular hospital rooms. At this point, in an exemplary embodiment a member of the surgical team (such as the scrub nurse) may send a medical procedure status update, notifying a surgical team to perform in the operating room following the present surgery that the preceding surgical team in current use of the operating room is prepared to begin the medical treatment. This may put the following surgical team on notice that the operating room will be available shortly, and that the subsequent surgical team may begin preparing their patient for surgery or other such preparations may be commenced. This may contribute to decreasing the costs of a medical procedure as the efficiency of time management is maximized. Moreover, a status update message may be sent to any surgical personnel needed during the surgery, such as if there is a special scenario where an extra surgeon or extra scrub nurse is needed.

When the medical procedure (for example a surgery) is to begin at step 210, anesthesia may be administered 236. The anesthesia may be local or general. Depending on the type of surgery, and thus the type of anesthesia used, the patient may remain conscious or become unconscious and paralyzed during the surgery. If unconscious, the patient may be intubated and placed on a medical ventilator. To begin treatment, the incision may be made to access the surgical site 238. Blood vessels may be clamped to prevent bleeding and retractors may be used to expose the site or keep the incision open. The surgeon may then begin work to correct the problem in the body 240. An exemplary embodiment may be performed at this stage—such as: the surgical team may notify a subsequent surgical team when anesthesia has been administered, when the first incision has been made, and/or updates of different stages of a specific surgery type to maximize time efficiency.

For patient treatment 210, steps of the surgical procedure itself may vary depending on the surgery being performed. For example, in bypass surgery a graft may be performed where pieces of tissue are severed from a different part of the same (or possibly a different) body. Clogged blood vessels may then be bypassed with said graft from another part of the body. In an exemplary embodiment the surgical team may provide updates of the time-line of the surgery. In one embodiment special updates may be issued for unanticipated events. One example of these special updates may be if there is excessive bleeding, and the surgery will take longer than previously predicted. Another update may be sent if the surgery is going smoothly, and the surgeon predicts the surgery will be finished sooner than expected.

After patient treatment 210, patient observation begins at step 212. The incision may be closed 242 and the anesthetic agents may be stopped and/or reversed 244. The anesthesiologist may monitor the patient's recovery from anesthesia. The patient may be taken off ventilation. The patient is then transferred to a post anesthesia care unit where they may be closely monitored 246. When judged to have recovered, the patient may be transferred to a surgical ward or be discharged. Other follow-up studies, further treatment, or rehabilitation may be prescribed. In an exemplary embodiment the surgical technician may be notified through the medical communications system that the patient is ready for transfer to another ward, or to be discharged. In another exemplary embodiment, a member of the surgical team may notify following surgical team members that the medical procedure has been completed, and/or that the room is currently being cleaned for further use. In yet another exemplary embodiment medical personnel related to follow-up treatment may be notified of the patient's status for continued care.

The surgical technician may then oversee set-up and preparation of the medical procedure site (which may be an operating room) 214 for the following surgical team. The room may be cleaned again for the next surgical team. The instruments may be sterilized 248 and the room may be cleaned by hospital maintenance 250. In an exemplary embodiment, when the medical procedure site is fully prepared the surgical technician may notify the following surgical team such that they are aware of its availability and may proceed with the next surgery immediately.

A typical example of the flow of information in one exemplary embodiment of the present invention is that the reception desk employee may notify the surgical or scrub nurse when the patient has arrived by activating that status message through the medical communication system. In another exemplary embodiment, when the patient is prepared for surgery by the surgical nurse, the surgical nurse may notify the surgeon, the circulating nurse, the surgical technician, and/or the anesthesiologist that the patient has arrived and is prepared for surgery by activating the medical communication system to send a status message to the surgical team once when the patient has arrived, and once again when the patient is prepared for surgery. In still another exemplary embodiment status messages may be sent at various stages during the medical procedure, and status messages may be sent regarding the patient's status once the medical procedure is completed. Yet another status update may be sent once the medical procedure site is prepared for subsequent treatment.

Figure 3:
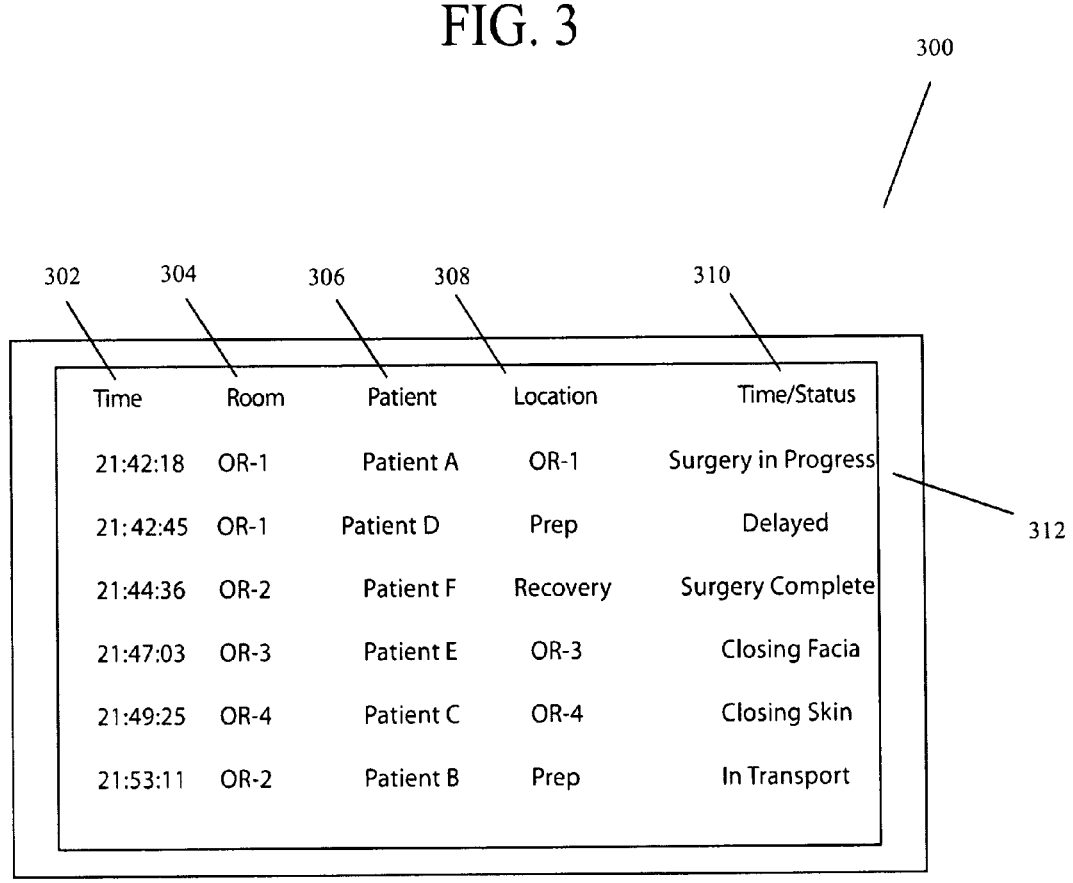
FIG. 3 illustrates a sample display for a preferred embodiment.

FIG. 3 illustrates a sample display 300 for a preferred embodiment. The figure illustrates display 300 and information labels, such as time 302, room number 302, patient name or number 306, medical procedure location 308, and the status of the medical procedure 310. Status information 312 is also shown. In other embodiments, however, other information may be displayed such as the name of the doctor performing the procedure, or a "team number" assigned to the medical procedure team. The type of procedure being performed may also be used. It is important to note the information labels are an exemplary embodiment, and should not be read to limit the present invention. In an exemplary embodiment of the present invention, the display may be presented on a hand-held device for a specific recipient or may be visible on a large screen in an open viewing area, such as a nurse's station. In other exemplary embodiments, the display may depict the medical treatment status message, the time of transmission, or the surgical team and/or operating room with which the message corresponds. In still another exemplary embodiment, the color of the display may change, or the message may blink or flash, when a specifically-intended recipient sends transmission that the status information has been received and acknowledged.

Figure 4A:
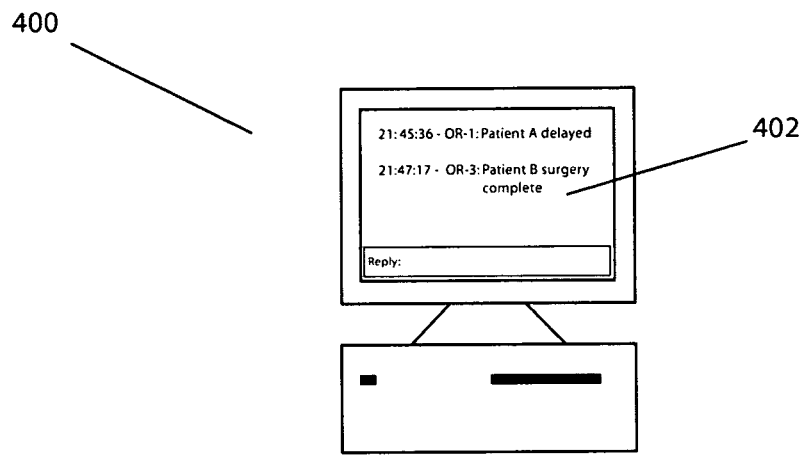
FIGS. 4(a)-(b) illustrate preferred embodiments of devices capable of receiving transmitted status messages.
Figure 4B:
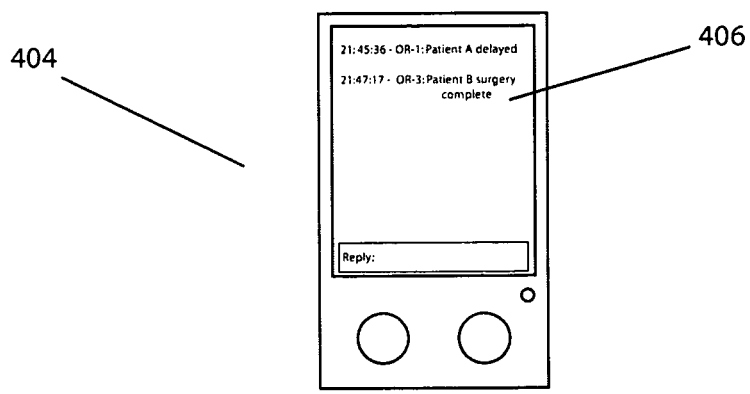

FIGS. 4(a)-(b) illustrate preferred embodiments of devices capable of receiving transmitted status messages. In one embodiment the device may be wired, and transmission may be sent to a personal computer 400. The status message may then be displayed on the monitor screen 402. In another embodiment the device may be wireless. In a preferred embodiment, the device may be wireless and portable, such as a hand-held device 404. The status message may then be displayed on the face of the hand-held device 406. An exemplary hand-held device 404 may include a cellular phone, PDA, notebook computer, or another wireless and portable device.

The transmission of status messages may be performed by a plurality of devices. Preferred embodiments of devices capable of transmitting status messages may include a user interface for the input of the status message, and a transmitter for transmission of the status message. These devices may be either wired or wireless. In various embodiments, transmission devices may be portable or stationary.

Figure 5A:
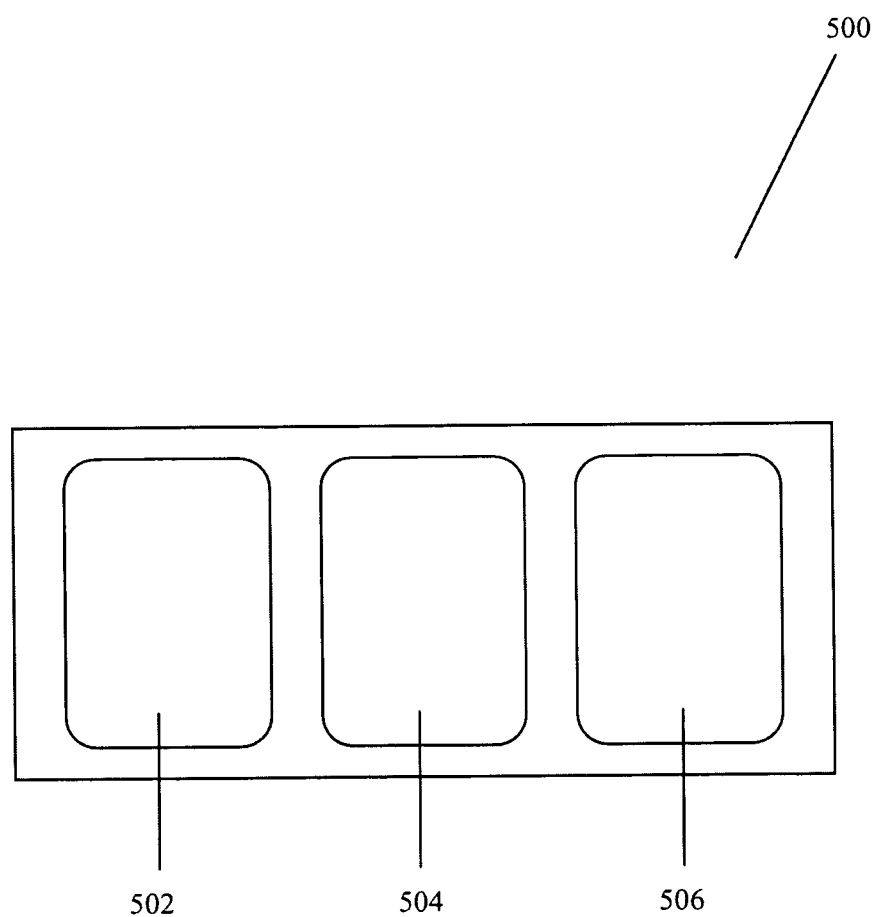
FIG. 5(a) illustrates a preferred embodiment of a pedal device adapted to send codes for respective stages of medical procedure performance.

FIG. 5(a) illustrates a preferred embodiment of a pedal device 500 adapted to send codes for respective stages of medical procedure performance. The exemplary embodiment illustrates a transmission device comprising a pedal. However, these devices may be embodied in a variety of manners, such as a wall panel, or hand-held device similar to a remote control, or a device that may be actuated by the user's elbow.

In one embodiment the device may be programmable, such that an input may be coordinated to correspond to a specific code. Thus, when a specific area of pedal device 500 is compressed, 502, 504, or 506, a uniquely programmed code may be sent. The uniquely programmed code may coordinate with a specific status message, which may then be displayed on a reception device. If pedal device 500 is programmable, the device may be arranged in the manner of the users' preference. In a preferred embodiment of the present invention, pedal device 500 may be pre-programmed. Thus, for a pre-programmed device 500, when a specific area of pedal device 500 is compressed, such as 502, 504, or 506, a pre-programmed code may be sent. The pre-programmed code may coordinate to a specific status message, which may then be displayed on a reception device in correlation to the pedal unit compressed.

Figure 5B:
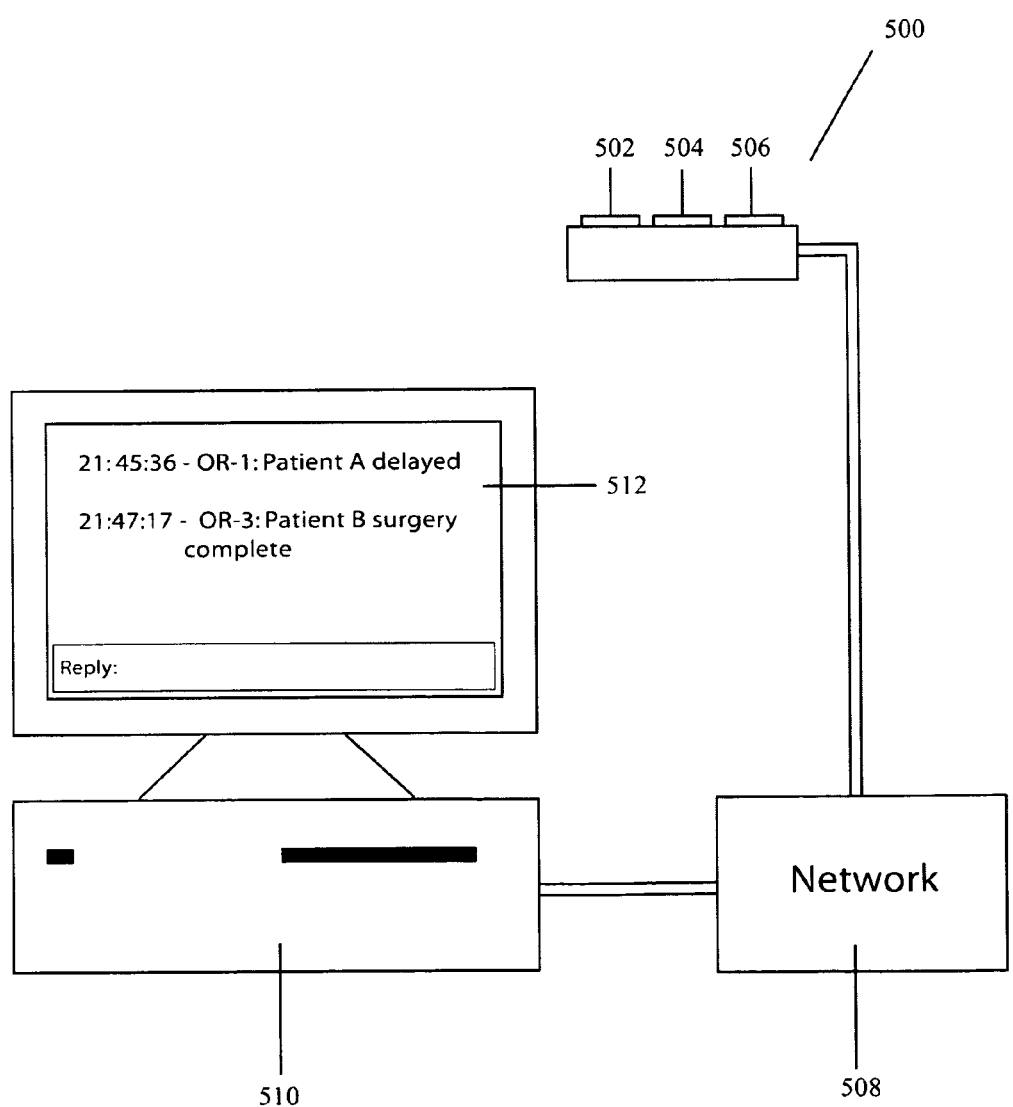
FIG. 5(b) illustrates the connection between the pedal device and the computer and computer network adapted to transmit status information for medical procedures.

FIG. 5(b) illustrates the connection between pedal device 500, computer network 508, and computer 510 adapted to transmit status information for medical procedures. In one embodiment, pedal device 500 may be programmable based upon user preferences, but in another embodiment pedal device 500 may be pre-programmed. Based upon the device programming, in a preferred embodiment, when a specific area of the pedal 502, 504, or 506 is depressed, a code coordinating with that area may be sent to a network interface 508. The network may then connect to a computer 510 and may transmit and distribute the real-time status information. Computer 510 may then be adapted to translate said codes into real-time status information to be displayed on the computer's main screen 512. It is important to note that this is one embodiment, and in another embodiment the network may not have a centralized hub, and may go directly to an intended recipient with a peer-to-peer connection. In one embodiment, recipients may be specifically selected, or the information may be sent through a general broadcast. Another embodiment of the present invention may include reception devices that are centrally-located community display boards, or yet another embodiment may include wireless reception devices that may be hand-held such that specific individuals may receive medical procedure updates regardless of where the individual may be located at the time of transmission. Exemplary embodiments may encompass transmission being activated by several people—in fact any member of the medical procedure, or any personnel interested in the status of the medical procedure may send or receive status updates.

Figure 5C:
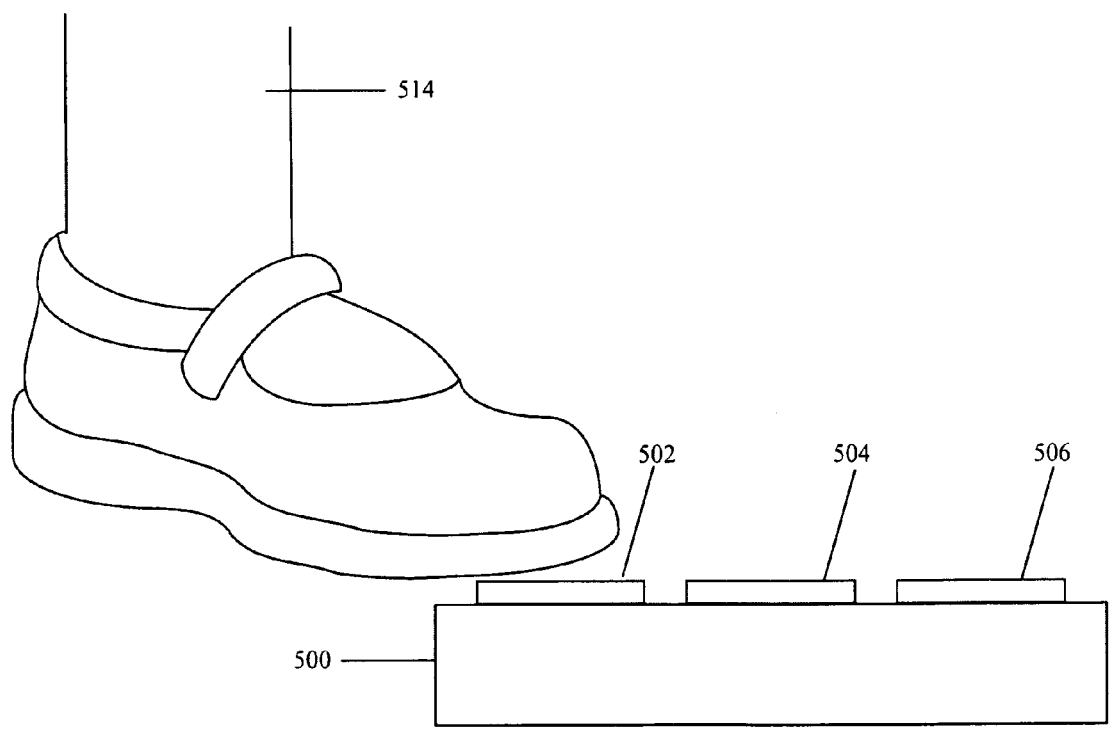
FIG. 5(c) illustrates a preferred embodiment of a pedal device adapted to be specifically activated by foot compressions.

FIG. 5(c) illustrates a preferred embodiment of a pedal device 500 adapted to be specifically activated by foot compressions. Different compressible units 502, 504, or 506 may be coordinated to specific status messages. Therefore, when a user compresses a specific unit such as 502 with their foot 514, a medical update status message corresponding to unit 502 may be transmitted to recipients. In this way, the integrity of sterile techniques and procedures may be maintained while messages are transmitted, without the necessity for taking the time to enter the status update manually.

Alternatively, devices that transmit status messages may function without user input. Such devices may comprise a sensor device, and a transmitter for transmission of the status message. Such sensor devices may function by sensing an environmental or medical procedure condition through magnetism, weight compression, electronic signal, radio frequency, or some other means. In an exemplary embodiment, a device may transmit a status message that a stage of a medical procedure has been completed when a doctor picks up or places down a surgical tool upon the surgical instrument table. In such an exemplary embodiment, the removal or placement of a surgical instrument upon the surgical instrument table may be detected through magnetism or weight compression. When the removal or placement of the surgical instrument is detected, the device may then transmit pre-defined codes to pre-designated recipients. Consequently, a status message may be specifically tailored to reflect specific information about the medical procedure depending upon what condition is met or sensor is activated.

A medical real-time status update communication method and device have been described. The foregoing description of the various exemplary embodiments of the invention has been presented for the purposes of illustration and disclosure. It is not intended to be exhaustive or to limit the invention to the precise form disclosed. Many modifications and variations are possible in light of the above teaching. It is intended that the scope of the invention not be limited by this detailed description, but by the claims and the equivalents to the claims.

What is claimed is:

1. A medical communications system comprising:
a pedal device adapted to send a first set of codes for respective stages of a medical procedure;
a sensor device for sensing a specific stage of a medical procedure, wherein the sensor device is configured to:
detect a displacement of a medical instrument on a medical instrument table using weight compression whenever a medical personnel picks up or places down the medical instrument on the medical instrument table, and
transmit a status message indicating that the stage of the medical procedure has been completed in response to detecting the displacement of the medical instrument,
a computer adapted to translate said set of codes into real-time status information; and
a network interface that transmits and distributes the status message and said real-time status information to one or more mobile devices.

2. The system of claim 1, wherein said pedal includes buttons related to the set of codes such that respective stages of the medical procedure are transmitted with respect to the button pressed.

3. The system of claim 1, wherein said pedal is programmable.

4. The system of claim 1, wherein said pedal is operable by foot depression.

5. The system of claim 1, wherein said sensor device is wireless.

6. A medical communications system used for scheduling medical procedures in an operating room, comprising:
a pedal, responsive to a medical personnel, adapted to generate a first set of codes indicative of specific stages of a medical procedure performed on a patient by said medical personnel in a particular operating room;
a sensor device configured to detect a displacement of a medical instrument on a medical instrument table using weight compression whenever the medical personnel picks UP or places down the medical instrument on the medical instrument table, and transmit a status message indicating that the stage of the medical procedure has been completed in response to detecting the displacement of the medical instrument;
a computer adapted to translate the set of codes into detailed real-time status information concerning the specific stages of the medical procedure performed in the operating room;
a display adapted to generate the real-time status information in a tabulated form, wherein the real-time status information includes:
a time associated with the specific stage of the medical procedure,
an identity of the operating room,
an identity of the patient in the operating room,
a location associated with the operating room, and
the specific stage of the medical procedure; and
a network interface that transmits and distributes the status message and said real-time status information to one or more mobile devices.

7. The medical communications system of claim 6, wherein the specific stage includes the patient's arrival.

8. The medical communications system of claim 6, wherein the specific stage includes set-up and preparation of the operating room.

9. The medical communications system of claim 6, wherein the specific stage includes preparation of the patient.

10. The medical communications system of claim 6, wherein the specific stage includes preparation of a surgical team.

11. The medical communications system of claim 6, wherein the specific stage includes treatment of the patient.

12. The medical communications system of claim 6, wherein the specific stage includes observation of the patient.

13. The medical communications system of claim 6, wherein the specific stage includes a clean-up of the operating room.

14. A medical communications system comprising:
a sensor device for sensing a completion of a stage of a medical procedure, the sensor device configured to:
detect a displacement of a medical instrument on a medical instrument table using weight compression whenever a medical personnel picks UP or places down the medical instrument on the medical instrument table, and
transmit a status message indicating that the stage of the medical procedure has been completed in response to detecting the displacement of the medical instrument;
a computer adapted to distribute the status message to one or more display devices; and
a pedal device, in communication with the computer, adapted to generate a set of codes indicative of specific stages of the medical procedure, wherein the pedal device includes buttons related to the codes such that respective stages of the procedure are transmitted with respect to the button pressed, and wherein the computer is further adapted to translate the set of codes from the pedal into real-time status information concerning the medical procedure.

15. The system of claim 14, wherein one of the one or more display devices is configured to generate the real-time status information in a tabulated form.

16. The system of claim 14, wherein the real-time status information includes:
a time associated with the specific stage of the medical procedure;
an identity of the operating room;
an identity of the patient in the operating room;
a location associated with the operating room; and
the specific stage of the medical procedure.

* * * * *